US012245711B2

(12) United States Patent
Varghese (10) Patent No.: US 12,245,711 B2
(45) Date of Patent: Mar. 11, 2025

(54) BIO-DEGRADABLE MEANS FOR USE AS DRINKING STRAW, STIRRER AND CHOP STICK AND A METHOD THEREOF (71) Applicant: EVLOGIA ECO CARE PRIVATE LIMITED, Karnataka (IN)

(72) Inventor: Saji Varghese, Bangalore (IN)

(73) Assignee: EVLOGIA ECO CARE PRIVATE LIMITED, Bangalore (IN)

( * ) Notice: Subject to any disclaimer, the term of this patent is extended or adjusted under 35 U.S.C. 154(b) by 770 days.

(21) Appl. No.: 17/257,263

(22) PCT Filed: Aug. 27, 2019

(86) PCT No.: PCT/IN2019/050621
§ 371 (c)(1),
(2) Date: Dec. 30, 2020

(87) PCT Pub. No.: WO2020/044370
PCT Pub. Date: Mar. 5, 2020

(65) Prior Publication Data
US 2021/0362447 A1 Nov. 25, 2021

(30) Foreign Application Priority Data
Aug. 29, 2018 (IN) .............................. 201841032438

(51) Int. Cl.
*A61K 31/55* (2006.01)
*A47G 21/06* (2006.01)
*B29D 23/00* (2006.01)
*C07K 16/28* (2006.01)
*C07K 16/30* (2006.01)
(Continued)

(52) U.S. Cl.
CPC ............ *A47G 21/103* (2013.01); *A61K 31/55* (2013.01); *B29D 23/00* (2013.01); *C07K 16/2803* (2013.01); *C07K 16/30* (2013.01); *C07K 16/462* (2013.01); *A47G 21/18* (2013.01); *A61K 45/06* (2013.01); *B29K 2001/00* (2013.01)

(58) Field of Classification Search
CPC .............................. A47G 21/103; A47G 21/18
See application file for complete search history.

(56) References Cited

U.S. PATENT DOCUMENTS

2002/0134850 A1 9/2002 Hollenberg

FOREIGN PATENT DOCUMENTS

| CN | 201219782 Y | 4/2009 |
| IN | 201741041171 | 12/2017 |

(Continued)

*Primary Examiner* — Qingzhang Zhou
(74) *Attorney, Agent, or Firm* — Maschoff Brennan (57) ABSTRACT Bio-degradable means (100) for use as drinking straw, stirrer and chop stick and a method (200) for making the bio-degradable means (100) is provided. The bio-degradable means (100) includes at least one dried leaf strip (100S) configured to be at least one of straight rolled and spiral rolled along an entirety of an elongated guide member R to facilitate formation of an elongated bio-degradable means (100). The dried leaf strip (100S) is at least one of a coconut tree leaf strip, palm tree leaf strip and a plantain leaf strip. A bonding agent is applied at at least one edge portion of each dried leaf strip (100S) with respect to a length wise direction of the dried leaf strip (100S) to maintain the elongated bio-degradable means (100) in rolled position.

9 Claims, 7 Drawing Sheets (51) Int. Cl.
*C07K 16/46* (2006.01)
*A47G 21/18* (2006.01)
*A61K 45/06* (2006.01)
*B29K 1/00* (2006.01)

(56) References Cited

FOREIGN PATENT DOCUMENTS

| | | |
|---|---|---|
| WO | 1996020604 A1 | 7/1996 |
| WO | 1997032717 A1 | 9/1997 |
| WO | 2009011815 A1 | 1/2009 |
| WO | WO2017018639 A1 * | 2/2017 |

* cited by examiner

BIO-DEGRADABLE MEANS FOR USE AS DRINKING STRAW, STIRRER AND CHOP STICK AND A METHOD THEREOF

TECHNICAL FIELD

The embodiments herein relate to a bio-degradable means for use as at least one of a drinking straw, a stirrer and a chop stick, and a method for making the bio-degradable means.

BACKGROUND

Generally, a drinking straw is an elongated tube that allows a user to draw fluid from tender coconuts, fluid containers and the like to consume drinkables thereof. Mostly, drinking straws are made of plastic. Though the manufacturing of plastic straws incurs less cost, plastic straws account for a significant amount of un-recycled plastic waste, and contribute to plastic pollution in the ocean. Some drinking straws are made of paper. Though paper straws are bio-degradable, the manufacturing of paper straws incurs high cost. Further, a coffee stirrer is an elongated metallic rod that is used to stir the coffee in a mug or any other vessel. Though the metallic coffee stirrer is durable, the manufacturing of metallic coffee stirrer incurs high cost. Furthermore, chop stick are a pair of equal length sticks that are used as kitchen and eating utensils. Mostly chop sticks are made of bamboo and wood. Though bamboo and wood chop sticks are bio-degradable, relatively inexpensive, low in temperature conduction and provide good grip for holding food, the bamboo and wood chop sticks can warp and deteriorate with continued use.

Therefore, there exists a need for a bio-degradable means for use as at least one of a drinking straw, a stirrer and a chop stick, which obviates the aforementioned drawbacks. Further, there exists a need for a method for making a bio-degradable means, which obviates the aforementioned drawbacks.

OBJECTS

The principal object of an embodiment of this invention is to provide a bio-degradable means for use as at least one of a drinking straw, a stirrer and a chop stick.

Another object of an embodiment of this invention is to provide a method for making a bio-degradable means being used as at least one of a drinking straw, a stirrer and a chop stick.

Another object of an embodiment of this invention is to provide a bio-degradable means for use as at least one of a drinking straw, a stirrer and a chop stick, where the making of the bio-degradable means incurs less cost.

These and other objects of the embodiments herein will be better appreciated and understood when considered in conjunction with the following description and the accompanying drawings. It should be understood, however, that the following descriptions, while indicating embodiments and numerous specific details thereof, are given by way of illustration and not of limitation.

Many changes and modifications may be made within the scope of the embodiments herein without departing from the spirit thereof, and the embodiments herein include all such modifications.

BRIEF DESCRIPTION OF DRAWINGS

The embodiments of the invention are illustrated in the accompanying drawings, throughout which like reference letters indicate corresponding parts in the various figures. The embodiments herein will be better understood from the following description with reference to the drawings, in which.

DETAILED DESCRIPTION

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

The embodiments herein achieve a bio-degradable means for use as at least one of a drinking straw, a stirrer and a chop stick and a method for making the bio-degradable means. Referring now to the drawings, and more particularly to FIGS. 1 through 7, where similar reference characters denote corresponding features consistently throughout the figures, there are shown embodiments.

Figure 1:
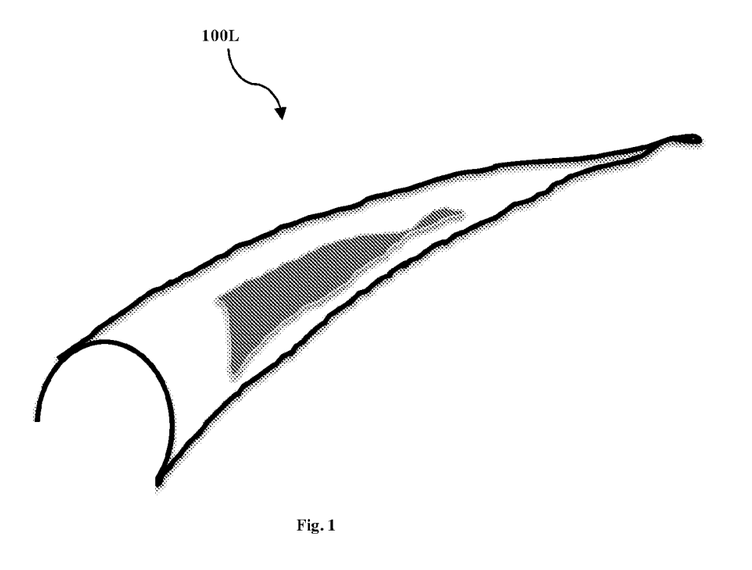
FIG. 1 depicts a perspective view of a dried leaf which is used for making a bio-degradable means being used as at least one of a drinking straw, a stirrer and a chop stick, according to an embodiment of the invention as disclosed herein.
Figure 2:
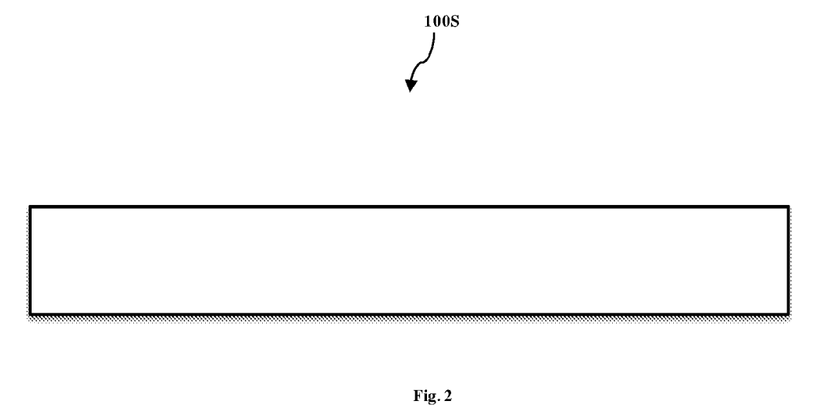
FIG. 2 depicts a front view of a dried leaf strip which is cut from a dried leaflet that is separated from the dried leaf midrib, according to an embodiment of the invention as disclosed herein.
Figure 3:
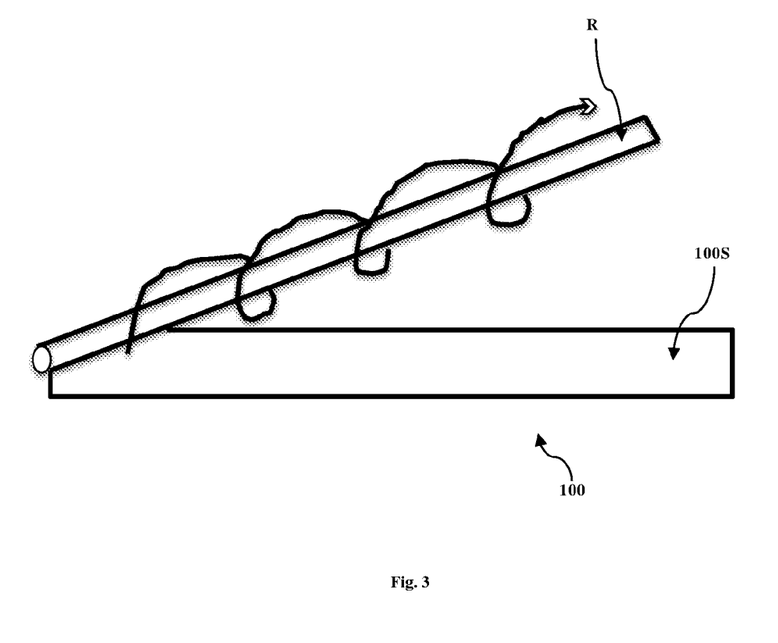
FIG. 3 depicts a perspective view of the dried leaf strip being spiral rolled along an entirety of an elongated guide member to facilitate formation of the spiral rolled bio-degradable means, according to an embodiment of the invention as disclosed herein.
Figure 4:
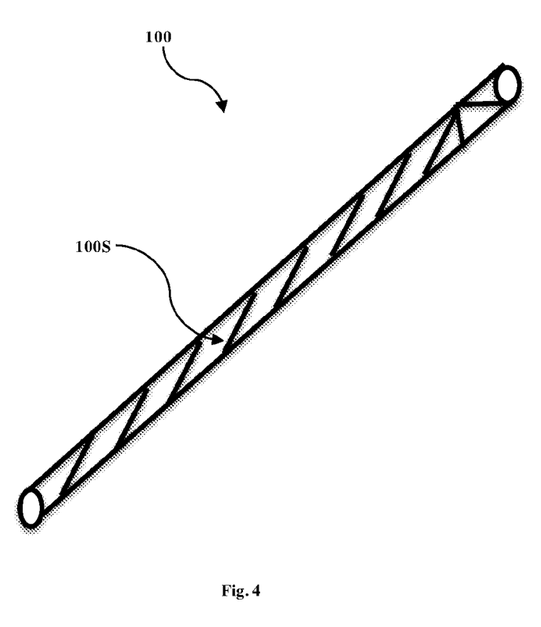
FIG. 4 depicts a perspective view of the spiral rolled bio-degradable means, according to an embodiment of the invention as disclosed herein.
Figure 5:
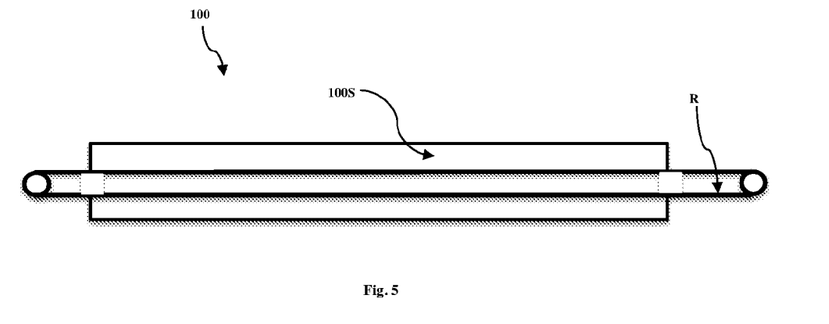
FIG. 5 depicts a perspective view of the dried leaf strip being straight rolled along an entirety of the elongated guide member to facilitate formation of the straight rolled bio-degradable means, according to an embodiment of the invention as disclosed herein.
Figure 6:
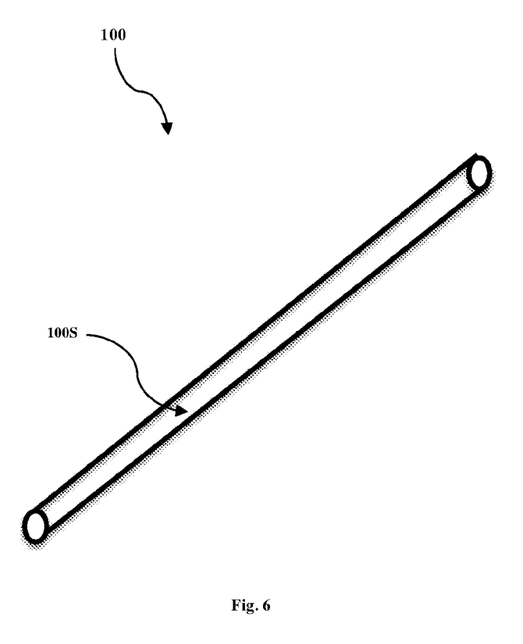
FIG. 6 depicts a perspective view of the straight rolled bio-degradable means, according to an embodiment of the invention as disclosed herein.

FIG. 1 depicts a perspective view of a dried leaf 100L which is used for making a bio-degradable means 100 being used as at least one of a drinking straw, a stirrer and a chop stick, according to an embodiment of the invention as disclosed herein. FIG. 2 depicts a front view of a dried leaf strip 100S which is cut from the dried leaflet that is separated from the dried leaf midrib, according to an embodiment of the invention as disclosed herein. In an embodiment, the bio-degradable means 100 (as shown in FIG. 4 and FIG. 6) have at least one dried leaf strip 100S adapted to be rolled along an elongated guide member R to facilitate formation of an elongated tubular bio-degradable means 100. It is also within the scope of the invention to provide the elongated bio-degradable means 100 in any other shape and configuration without otherwise deterring the intended function of the bio-degradable means 100 as can be deduced from the description and corresponding drawings. The elongated guide member R is at least an elongated rod. It is also within the scope of the invention to provide the elongated guide member R in form an elongated tube. In an embodiment, the dried leaf strip 100S is configured to be spiral rolled along an entirety of the elongated guide member R at a predefined angle to facilitate formation of the spiral rolled elongated tubular bio-degradable means 100 (as shown in FIG. 4). The dried leaf strip 100S is configured to be straight rolled along an entirety of the elongated guide member R to facilitate formation of the straight rolled elongated tubular bio-degradable means 100 (as shown in FIG. 6). The dried leaf strip 100S is cut from a dried leaf 100L. In an embodiment, the bio-degradable means 100 is at least a bio-degradable drinking straw. In one embodiment, the dried leaf 100L is at least a coconut tree leaf. In another embodiment, the dried leaf 100L is at least one of a palm tree leaf and a plantain leaf. It is also within the scope of the invention to consider the dried leaf 100L as any other tree leaf or any other plant leaf. In another embodiment, the bio-degradable means 100 is at least one of a bio-degradable stirrer and a bio-degradable chop stick.

The formation of dried leaf strip 100S is as follows. At least one dried leaf 100L is cleaned in running water to remove dust and foreign particles from the dried leaf 100L. Thereafter, the dried leaf 100L is exposed to at least one of boiling and steaming to sterilize the dried leaf 100L and to make the dried leaf 100L flexible which facilitates in rolling of the elongated tubular bio-degradable means 100 and also to generate natural wax in the flexible dried leaf 100L. Thereafter, a plurality of dried leaflets is separated from a midrib (not shown) of the flexible dried leaf 100L. Thereafter, each dried leaflet is cut into a plurality of dried leaf strips 100S. Each dried strip 100S is buffed to bring the shine out of the dried leaf strip 100S.

A bonding agent is applied at at least one edge portion of each dried leaf strip 100S with respect to a length wise direction of the waxed dried leaf strip 100S and the edge portion of said dried leaf strip 100S is joined with corresponding portion of said dried leaf strip 100S so that the bonding agent attaches the edge portion with corresponding portion of said dried leaf strip 100S to maintain the elongated tubular bio-degradable means 100 in rolled position. The bonding agent is dried out in elongated tubular bio-degradable means 100. The bonding agent is at least a food grade water resistant adhesive. In one embodiment, the bonding agent is bio-degradable. In another embodiment, the bonding agent is non-biodegradable. The edge portion of the dried leaf strip 100S is joined so that the bonding agent attaches the edge portion with corresponding portion of the dried leaf strip 100S to maintain the elongated tubular bio-degradable means 100 in rolled position. Both ends of the elongated tubular bio-degradable means 100 are cut to facilitate uniform finishing of the elongated tubular bio-degradable means 100. Laser engraving logo is made on each elongated tubular bio-degradable means 100. The plurality of elongated tubular bio-degradable means 100 is packaged in at least one box.

Figure 7:
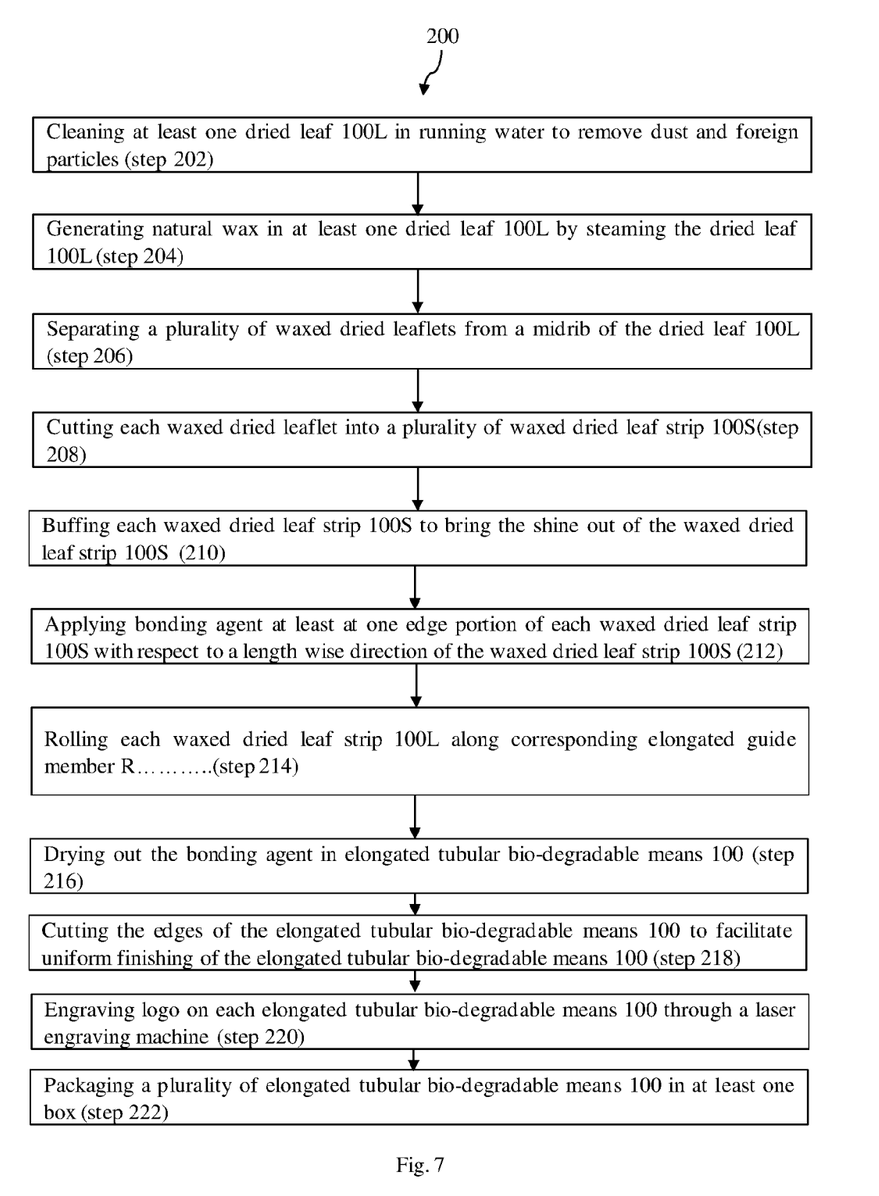
FIG. 7 depicts a flowchart showing the steps of a method for making a bio-degradable means being used as at least one of a drinking straw, a stirrer and a chop stick, according to an embodiment of the invention as disclosed herein.

FIG. 7 depicts a flowchart showing the steps of a method 200 for making a bio-degradable means 100 being used as at least one of a drinking straw, a stirrer and a chopstick, according to an embodiment of the Invention as disclosed herein. For the purpose of this description and ease of understanding, the method 200 for making the bio-degradable means 100 is explained herein below with reference to a bio-degradable drinking straw. However, it is also within the scope of the invention to practice/implement the entire steps of the method 200 or with omission of at least one step of the method 200 or with any addition of at least one step to the method 200 for making a bio-degradable drinking straw or a bio-degradable stirrer or a bio-degradable chop stick. In an embodiment, the method 200 for making the bio-degradable means 100 is as follows. The method 200 comprises, cleaning at least one dried leaf 100L in running water to remove dust and foreign particles (step 202), exposing at least one dried leaf 100L to at least one of steaming and boiling to form a flexible dried leaf 100L (step 204), separating a plurality of dried leaflets from a midrib of the flexible dried leaf 100L (step 206), cutting each dried leaflet into a plurality of dried leaf strip 100S (step 208), buffing each dried leaf strip 100S to bring the shine out of the dried leaf strip 100S (step 210), applying bonding agent at at least one edge portion of each dried leaf strip 100S with respect to a length wise direction of the dried leaf strip 100S (step 212), rolling each dried leaf strip 100L along corresponding elongated guide member R and joining the edge portion of the dried leaf strip 100S so that the bonding agent attaches the edge portion with corresponding portion of the dried leaf strip 100S to facilitate formation of corresponding elongated tubular bio-degradable means 100 (step 214), drying out the bonding agent in elongated tubular bio-degradable means 100 (step 216), cutting both ends of the elongated tubular bio-degradable means 100 to facilitate uniform finishing of the elongated tubular bio-degradable means 100 (step 218), engraving logo on each elongated tubular bio-degradable means 100 through a laser engraving machine (step 220) and packaging a plurality of elongated tubular bio-degradable means 100 in at least one box (step 222). In one embodiment, the dried leaf 100L is at least a coconut tree leaf. In another embodiment, the dried leaf 100L is at least one of a palm tree leaf and a plantain leaf. It is also within the scope of the invention to consider the dried leaf 100L as any other tree leaf or any other plant leaf. In one embodiment, the elongated tubular bio-degradable means 100 is at least bio-degradable drinking straw. In another embodiment, the elongated tubular bio-degradable means 100 is at least one of a bio-degradable stirrer and a bio-degradable chop stick.

Therefore, a bio-degradable means 100 for use as at least one of a bio-degradable drinking straw, a bio-degradable stirrer and a bio-degradable chop stick and a method 200 for making the bio-degradable means 100 is provided.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of embodiments, those skilled in the art will recognize that the embodiments herein can be practiced with modification within the spirit and scope of the embodiments as described herein.

I claim:

1. A method (200) for making an elongated bio-degradable means (100), said method (200) comprising:
   providing a dried leaf (100L);
   exposing the dried leaf (100L) to at least one of steaming and boiling to form a dried leaf (100L) and to generate natural wax in the dried leaf (100L);
   separating a plurality of dried leaflets from a midrib of the dried leaf (100L);
   separating at least one dried leaf strip (100S) from at least one dried leaflet of the plurality of dried leaflets;
   applying a bonding agent comprising a food grade water resistant adhesive, at least at one edge portion of the at least one dried leaf strip (100S) with respect to a lengthwise direction of the at least one dried leaf strip (100S); and
   rolling the at least one dried leaf strip (100S) along an elongated guide member (R) and joining the edge portion of the at least one dried leaf strip (100S) so that the bonding agent attaches the edge portion with a corresponding portion of the at least one dried leaf strip (100S) to form the elongated bio-degradable means (100) comprising at least one of a drinking straw, a stirrer, and a chop stick.

2. The method (200) as claimed in claim 1, wherein said separating the at least one dried leaf strip (100S) from the at least one dried leaflet includes cutting the at least one dried leaflet into the at least one dried leaf strip (100S) after separating the at least one dried leaflet from the midrib.

3. The method (200) as claimed in claim 1, comprising cleaning the dried leaf (100L) in water to remove dust and foreign particles prior to said exposing the dried leaf (100L) to at least one of steaming and boiling to form at least one dried leaf (100L).

4. The method (200) as claimed in claim 1, comprising buffing the at least one dried leaf strip (100S) to bring the shine out of the dried leaf strip (100S) before rolling the at least one dried leaf strip (100S) along the elongated guide member (R) to form the elongated bio-degradable means (100).

5. The method (200) as claimed in claim 1, comprising drying out the bonding agent in the elongated bio-degradable means (100) after said rolling of the at least one dried leaf strip (100L) along the elongated guide member (R) and joining the edge portion of the dried leaf strip (100S) so that the bonding agent attaches the edge portion with the corresponding portion of the at least one dried leaf strip (100S) to form the elongated tubular bio-degradable means (100).

6. The method (200) as claimed in claim 1, comprising:
   cutting both ends of the elongated bio-degradable means (100) to provide uniform finishing to the elongated bio-degradable means (100); and
   packaging a plurality of elongated bio-degradable means (100) in at least one box.

7. The method (200) as claimed in claim 6, comprising:
   engraving logo on each of the elongated bio-degradable means (100) through a laser engraving machine prior to said packaging the plurality of elongated bio-degradable means (100) in the at least one box.

8. The method (200) as claimed in claim 7, wherein said dried leaf 100L) is at least a coconut tree leaf.

9. The method (200) as claimed in claim 8, wherein said at least one dried leaf (100L) is at least one of a palm tree leaf and a plantain leaf.

\* \* \* \* \*